United States Patent [19]

Ecanow

[11] Patent Number: 5,039,540
[45] Date of Patent: Aug. 13, 1991

[54] FREEZE DRY COMPOSITION AND METHOD FOR ORAL ADMINISTRATION OF DRUGS, BIOLOGICALS, NUTRIENTS AND FOODSTUFFS

[75] Inventor: Bernard Ecanow, Wilmette, Ill.

[73] Assignee: Neophore Technologies, Inc., Deerfield, Ill.

[21] Appl. No.: 393,582

[22] Filed: Aug. 14, 1989

[51] Int. Cl.$^5$ .................. A23L 3/44; A61H 47/42; A61H 47/36
[52] U.S. Cl. .................. 426/385; 514/774; 514/776; 514/777
[58] Field of Search ............ 426/385; 424/602, 617; 514/622, 774, 776, 777, 450

[56] References Cited

U.S. PATENT DOCUMENTS

| | | | |
|---|---|---|---|
| 473,331 | 4/1892 | McKay | 424/602 |
| 2,166,074 | 7/1939 | Reichel | 426/385 |
| 3,298,100 | 1/1967 | Bohrer | 426/385 |
| 4,537,883 | 8/1985 | Alexander et al. | 514/110 |
| 4,616,047 | 10/1986 | Lafon | 426/384 |
| 4,752,466 | 6/1988 | Saferstein | 424/46 |

FOREIGN PATENT DOCUMENTS

| | | | |
|---|---|---|---|
| 0017395 | 2/1980 | Japan | 514/777 |

OTHER PUBLICATIONS

Gstirner et al., Pharm. Ind. 1971, 33(10) 683–5.
Chemical Abstracts, vol. 76, 1972, Abs. 37407h.
Endo et al., Shigaku, 1979, 27(4) 1408–15.
Chemical Abstracts, vol. 42, 1990, Abstract 104745.
Wu, Zhileng Xuebao 1986 (4) 30–7 Chemical Abstracts, vol. 106, 1987, Abstract 178658r.

*Primary Examiner*—Muklund J. Shah
*Assistant Examiner*—E. C. Ward
*Attorney, Agent, or Firm*—Marshall, O'Toole, Gerstein, Murray & Bicknell

[57] ABSTRACT

A readily dissolvable carrier material having sufficient rigidity for administration of drugs, nutrients, vitamins, biologically-active materials, foodstuffs and combinations thereof capable of rapid dissolution by saliva, bodily fluids or other liquid comprising an interim skeletal structure of a water-soluble, hydratable gel or foam forming material, preferably a proteinaceous material, such as gelatin, that has been hydrated, rigidified, such as with maltodextrin, in the hydrated state and dehydrated to leave spaces in place of hydration water. On dissolution by saliva, bodily fluids or other liquids. The composition becomes a liquid system. While the oral route is preferred, other routes may be used to administer the compositions of this method.

12 Claims, No Drawings

FREEZE DRY COMPOSITION AND METHOD FOR ORAL ADMINISTRATION OF DRUGS, BIOLOGICALS, NUTRIENTS AND FOODSTUFFS

FIELD OF THE INVENTION

The present invention is directed to semi rigid or rigid, solid carriers having a high degree of void space for carrying drugs, biologically active materials, foodstuffs, e.g., nutrients, and any other medically useful materials or materials capable of sustaining human or animal life. More particularly, the present invention is directed to solid materials, capable of carrying drugs, nutrients and the like, and are capable of relatively immediate dissolution into liquid form upon contact with animal or human saliva or water for oral ingestion. In other embodiments, the solid carriers of the present invention are dissolvable and/or dispersible in aqueous liquids for liquid administration of drugs, nutrients and the like. In any embodiment, the compositions of the present invention are promptly available for adsorption by mammals and can be prepared in the form of tablets, granules, powders or in liquid form for administration to man and animals. In particular, the methods and compositions of the present invention are directed to a new freeze drying process to dehydrate hydrated gel and foam materials, particularly proteinaceous substances, thereby leaving porous solid materials capable of absorbing and adsorbing high percentages of drugs, nutrients, and the like, and capable of rapid dissolution in aqueous liquids or in the mouth of man and animals for prompt delivery of active materials to the bloodstream.

BACKGROUND OF THE INVENTION AND PRIOR ART

The method and compositions of the present invention are directed to an alternative method of drying drug and nutrient carriers that produce solid, rigid, but rapidly dissolvable drug and nutrient carriers capable of rapid liberation of the active component to the body in a method that yields new and unexpected results over extant methods of freeze drying.

In accordance with an important feature of the present invention, a composition of (1) a hydrogel or foamed, non-toxic, edible solid carrier material, such as a proteinaceous material, particularly gelatin or a gelatin derivative, e.g., gelatin; gelatin A; gelatin B, modified fluid gelatin, albumin, and the like; or hydrogels formed from materials such as acacia, tragatanth, and/or guar gum; or aqueous foams formed with any anionic, cationic or amphoteric surfactant, either synthetic or natural (biosurfactants) e.g., lecithin; together with (2) a non-toxic, edible, polysaccharide, capable of rigidifying the hydrogel or foam substance during dehydration thereof, for example, dextrin or a dextrin derivative, such as maltodextrin, can be dried in accordance with the present invention to leave a porous skeleton carrier, preferably of a proteinaceous material, capable of absorbing and/or adsorbing many times its weight in a drug and/or nutrient and the like.

In accordance with one important embodiment of the present invention, the solid, porous, skeletal carrier is formed by drying the fully hydrated gel or foam material from the gel or foamed state by transfer of water from the hydrated material to an alcohol solution, when both the hydrated gel or foam material and the alcohol are frozen or near freezing, without necessitating vacuum conditions, as needed for lyophilization.

A literature search of Chemical Abstracts 1975 to 1988 failed to reveal any reference which anticipates or suggests the water removal methods of this invention or the products produced by such methods.

Reference texts such as Remington's Pharmaceutical Sciences, 15th Edition, 1976, and Lachman et al, The Theory And Practice Of Industrial Pharmacy, Lea & Febiger, 1978, describe the process of lyophilization as a method to stabilize water and heat-sensitive drugs.

Patent references which include lyophilization in their respective methods are exemplified by Alexander U.S. Pat. No. 4,537,883; Lafon U.S. Pat. No. 4,537,883; Vendel U.S. Pat. No. 3,496,267 and Saferstein, et al U.S. Pat. No. 4,752,466. In each of these patents a method involving lyophilizing or freeze drying under vacuum conditions of unstable compositions is disclosed.

Aside from the common use of low temperature, the low temperature drying method of the present invention has very little similarity to the process of lyophilization. The differences of method and product between this invention and the well known lyophilization process will become more apparent hereinafter.

Lyophilization involves the use of mechanical equipment and control of vapor pressure to produce stabilized drugs. In contrast, the method of the present invention includes the use of an organic solvent and is based on the chemical processes of solubilization and dissolution to produce drug and nutrient delivery compositions, preferably under ambient pressure conditions.

SUMMARY OF THE INVENTION

In brief, the present invention is directed to compositions and methods providing porous solids and semi-solids that disintegrate virtually instantaneously when contacted by water, saliva, and aqueous solutions and dispersions and are particularly useful for the oral delivery and ingestion of drugs, nutrients and the like. As used in this disclosure, the term "drug" is used to mean any composition defined as a drug by the Food, Drug and Cosmetic Act and its amendments. Also, the terms "nutrients", "foods" and "foodstuffs" are used interchangeably and are used to mean any composition in liquid, solid or semi-solid form, without limit, or combinations thereof that are ingested and assimilated by an animal, particularly man, to maintain growth and life. These compositions which may be used singly or in any combination in conjunction with the disclosed delivery system include vitamins, minerals, essential and nonessential amino acids, cations, anions; and also fats, proteins and carbohydrates, without limit, including nutritive derivatives therefrom. For purposes of this specification, powdered, granular or other forms of beverages such as coffee, milk and the like are included as "food" compositions that can be prepared by the method of the present invention.

Finished products of this method may be in the form of tablets, powders, granules or liquid forms. Alternatively, finished products of the present invention in the form of powders or granules may be used to prepare emulsions and suspensions of drug, biologically active, medical or nutrient components.

In accordance with an important feature of the present invention, the methods of the present invention also produce useful freeze dried compositions of foods and drug compositions that are more stable, and more capable of dissolution and dispersion than those produced by other methods.

In accordance with an important feature of the present invention, a composition of (1) a hydrated gel or foam material and (2) a rigidifying agent for the gel or foam, is intimately contacted with an anhydrous organic liquid desiccant or solvent, such as anhydrous ethyl alcohol at a temperature of about 0° C. or below, until substantially all of the water is removed from the gel or foam material. To achieve the full advantage of the present invention, a homogeneous mixture of the gel or foam, together with the rigidifying agent for the gel or foam is immersed in the liquid desiccant until completely dehydrated.

To achieve the full advantage of the present invention, the component materials of the compositions are sequentially combined to produce interim products that are subjected to processes of solubilization and dissolution at temperatures of about 0° C. or below; preferably −10° C. or lower. An ice-dissolving anhydrous organic desiccant or solvent is used for dehydration in accordance with the preferred process of the present invention. The organic liquid water removal step removes the water from the composition being prepared and provides new and unexpected advantages in the finished products. The finished products in accordance with the method of the present invention are complete when from about 50% to about 100% by weight of the water of the hydrated gel or foam material of this method have been removed and transferred to the liquid desiccant.

In this method, the water-hydrated composition of a gel or foam material and a rigidifying agent therefor is frozen in a vessel suitable for maintaining temperatures of 0° C. or lower. The water removal steps may be repeated as often as is required to produce the required degree of dehydration.

To achieve the full advantage of the present invention, the finished proteinaceous compositions are completely dehydrated. On completion of the low temperature desiccant water-removal steps, the resulting product optionally can be further dried by any of the conventional methods to provide porous, solid drug, biological and/or nutrient delivery compositions in the form of tablets, granules and powders. If desired, the solids can be rehydrated to provide liquid delivery compositions.

Incorporation of a desired dose of the medical or nutritional component(s) in the porous solid carriers of the present invention and, as preferred, the addition of one or more flavoring agents complete the process of the present invention. The finished composition is suitable for oral administration and provide new and unexpected rapid liberation of the active component to the bloodstream of the recipient, particularly for epilingual administration. Since the compositions of the present invention disintegrate instantaneously in the mouth of the user, its contents are promptly available for absorption by the body. The finished products of this invention can be prepared as tablets, granules, powders, or as required as liquid forms such as suspensions and can be administered to man and animals. The methods and compositions of the present invention include methods to prepare freeze dried foodstuffs, and produce drug formulations that have improved stability and dispersibility in liquids.

In accordance with an important feature of the present invention, the compositions of the present invention have several advantages over conventional oral dosage forms: (1) the described formulations overcome objectionable tastes of incorporated nutrients and drugs, (2) as compositions of this invention disintegrate in the mouth or when, as an option, the formulations are prepared and taken in liquid form, such as suspensions, the compositions retain the characteristics of a stable suspension, and (3) the medical and nutrient components of the compositions are quickly available for absorption by the body. Finished products of this invention are ideal for persons who have difficulty ingesting drugs, biologically-active materials and nutrients which are commonly prepared as pills or tablets.

Accordingly, an object of the present invention is to provide a new and improved composition and method of manufacturing the composition comprising a porous, dehydrated solid carrier for drugs, biologically-active materials, nutrients, and the like that dissolves unexpectedly quickly in the mouth of the recipient for unexpectedly fast delivery of an active substance to the bloodstream.

Another object of the present invention is to provide a new and improved method of dehydrating a gel or foam solid material in gel or foam form such that the gel or foam substantially retains its gelled or foamed volume, and retains sufficient rigidity for handling and oral ingestion, but loses most or all of its water content to provide a solid, skeletal carrier that is exceptionally porous, capable of carrying many times its weight in a liquid active substance and capable of unexpectedly quick dissolution when orally ingested.

Another object of the present invention is to provide a new and improved gelatin-polysaccharide solid carrier, and method of manufacturing the solid carrier, for oral administration of active materials, such as drugs, biologically-active materials, foods, nutrients, vitamins and the like that is unexpectedly porous for receipt of the active material and is unexpectedly readily dissolvable in the mouth with saliva so that the active material is quickly assimilated through the mouth tissue or ingested into the GI tract.

Still another object of the present invention is to provide a new and improved method of freeze drying a hydrated, proteinaceous solid carrier material by intimately contacting the carrier, in substantially completely hydrated form, with an anhydrous desiccant, at 0° C. or below, to transfer water, in its frozen state, to the desiccant by sublimation or dissolution or solubilization.

The above and other objects and advantages of the present invention will be better understood in conjunction with the following detailed description.

DETAILED DESCRIPTION OF THE PREFERRED EMBODIMENT

The finished products of the present invention may be tablets, granules, powders or liquids. Tablets weighing about 100 to 150 mgs are preferred and may be of any size appropriate for oral administration. The compositions of this method may also be introduced into the body by other routes of administration. The disclosed carrier compositions may range in weight from about ½ gram too about 1200 mgs or more. The preferred method comprises the following steps: (1) Mix the following ingredients together: about 1 gram of flavored gelatin powder or other gelatin based equivalent, about 2 grams of maltodextrose, about 0.5 gram of gelatin A; about 2 grams of sucrose, optionally for palatability, and as preferred, about 1 gram, or other desired dosage of flavoring agents or sweeteners, such as ASPARTANE. The quantities may be adjusted as preferred by the formulator. After mixing these components, add distilled water in an amount that will make a final volume of about 100 ml., (2) heat while stirring the product of step (1) to about 60° C. or until the product becomes a visually clear solution. Next, (3) cool the product of step (2) to about 37° C. or less but preferably short of freezing, (4) rinse the molds to be used in forming the tablets of this method with any pharmaceutically acceptable coating liquid or lubricant, for example a solution of about 10% of a phospholipid, such as lecithin, in 190 proof grain alcohol. (5) Allow said molds to dry at ambient temperature.

Next, (6) fill each compartment of the mold with about 1 ml of the product of step (3). Store the product of step (7) at a temperature of 0° C. or lower for about 30 minutes or until the molded product (tablet) is frozen solid. (8) Remove the product of step (7) from storage and add that quantity of the drug, nutrient or combinations of each, preferably in powder or liquid form, e.g., as an aqueous solution, as preferred by the formulator, to the surface of each tablet within the mold. During this step the product should be protected from thawing. It is preferred that the product of step (8) is further processed with step (9) which comprises the following: remove the product of step (8) from storage and add from about ½ to about 3 mls of the product of step (1) to the upper surface of each frozen tablet in the mold. (10) Refrigerate the product of step (9) for about 30 minutes or more at 0° C. or lower. At the conclusion of step (10), if preferred, the product is removed from refrigeration and one or more flavoring agents are added to the surface of each frozen tablet in an amount ranging from a trace amount to one drop or more according to the preference of the formulator. At this point, the product comprises a semi-finished frozen tablet comprised of three layers.

At the option of the formulator, any one step or combination of process steps (1) through (10) and the related optional steps may be repeated to produce a semi finished product comprised of any number of layers as preferred by the formulator. On completion of step (10) the frozen tablets are removed from the mold and contacted with anhydrous ethyl alcohol, such as by immersion therein, preferably in an airtight container, step (11), as follows: The weight ratio of alcohol to the product can be approximately at least 10:1 alcohol to product, but is preferably about 40:1. This ratio may be adjusted as desired by the formulator. Next, place the product of step (10) in a suitable plastic container which may be a fine mesh plastic bag or a plastic bottle containing multiple holes of ½ mm or less or more and immerse in a container of anhydrous ethyl alcohol maintained at a temperature of −15° C. or lower. The water content of the alcohol can be measured before this step. Step (11) continues until the water content of the alcohol is about 2.5% or more. The process of step (11) is repeated using a fresh supply of anhydrous alcohol until about 100% of the water has been removed from the dosage form formulation. Next, place the tablets resulting from step (11) on blotting paper and transfer quickly to a vacuum chamber. (12) Vacuum dry the product of step (11) at ambient temperature until no odor of the ethyl alcohol remains.

In accordance with another important embodiment of the present invention the desired dose of the drug component is added by means of a pipette to the surface of each tablet after the product has been vacuum dried (step 12).

In accordance with another important embodiment of the present invention to produce the porous carrier materials, the hydrated composition of gel or foam material and gel or foam material rigidifying agent preferably in a frozen state, are spread on a preformed sheet. The sheet then is placed in a suitable freezer chest, preferably manufactured of porcelain. A container of anhydrous ethyl alcohol is also placed in the freezer chest in a weight ratio of at least 10:1 alcohol to wet product, e.g., 40:1. The temperature of the interior of the chest is maintained 15° C. or lower. The transfer of water from the starting materials to the alcohol is continued until about 90 to 100% of the solvent is transferred from the starting material to the anhydrous ethyl alcohol. The alcohol is replaced as required to complete the process of water removal. The processed material then is removed from the alcohol and dried by any pharmaceutically acceptable method to remove any alcohol which is present in the composition. The resulting product comprises a porous solid suitable for purposes of oral delivery of drugs, nutrients and the like. The product may be in tablet, powder or granular form, or reconstituted with water or other solvents for a liquid product.

The preferred procedure to add the drug or nutrient component to the porous solid delivery compositions described above is as follows: the component to be added is dissolved in any appropriate solvent including organic solvents. The dissolved drug is added dropwise by means of a hypodermic syringe or other similar device to the surface of the delivery composition in that amount that will give the desired dose to each product unit. The porous solid, its spaces now containing the drug or nutrient, then is dried using any conventional drying method to remove all traces of the solvent used in the formulation step. As preferred, the drug or nutrient component can be added to the interim product during earlier stages of preparing the porous solids. As preferred by the formulator, any flavoring agent may be added to the product by placing the agent in solution and adding that quantity of the flavoring agent that is preferred to the surface of the product by means of a hypodermic syringe or other similar device.

To prepare a granular form of the composition, the finished product is processed with a rotating granulator or other similar grinding equipment.

To prepare the powder form of this invention, a fine wire mesh with openings ranging from about 50 to 300 microns is used in place of the blister mold used to form tablets. The steps described to produce the tablet dosage form then are followed to produce the powder delivery form.

The starting materials of this method comprise the following compositions or combinations thereof any pharmaceutically acceptable gel or foam materials prepared from any surfactant, synthetic or biological, particularly proteinaceous materials such as gelatin, including types A and B, fluid gelatin and gelatin derivatives and albumin. Other suitable gel or foam forming compounds of biological or synthetic origin, used singly or in combination, include phospholipids, singly or in combination, particularly lecithin and coacervated egg lecithin.

Suitable rigidifying agents for such gels hydrogels, and foam forming materials include dextrin and dextrin derivatives, such as maltodextrin; carbohydrates including the mono-, di-, oligo- and other poly-saccharides. The monosaccarides include without limitation, dextrose, fructose and galactose and the sugar alcohols mannitol, xylitol and sorbitol; the disaccharides include without limitation sucrose, lactose and maltose. Oligosaccharides include polymers of the monosaccharide sugars, polysaccharides include dextrans having molecular weights ranging from 40,000 to 90,000. The amount of rigidifying agent is an amount sufficient to rigidify the gel or foam material, generally about 0.1 to 5 times the weight of the gel or foam forming material (dry basis).

The liquid, anhydrous organic desiccants or solvents used for dehydration include any organic solvent without limitation that will dissolve ice at about 0° C. or less, including acetone and the alcohols but especially ethyl alcohol about 150 to 200 proof; about 200 proof is preferred. As preferred, any pharmaceutically acceptable flavoring agent or combinations of such agents, including natural and synthetic flavoring agents, such as AS-PARTANE and flavor enhancing agents, such as the commercial product VELTOL (Pfizer); preservatives such as methyl paraben, propyl paraben and The oral delivery compositions of the present invention are useful to administer drugs in each of the following categories: drugs acting on the central nervous system; drugs acting at synaptic and neuroeffector sites; autacoids, cardiovascular drugs; drugs affecting renal function and electrolyte metabolism; drugs effecting uterine motility; antibiotic drugs; anti-fungal drugs; antineoplastic drugs; drugs acting on blood and blood forming organs and hormones. Nutrients that are useful for oral delivery in accordance with the present invention include water-soluble vitamins, such as the B vitamins and vitamin C; water soluble trace elements such as copper, selenium, calcium, chromium, zinc, magnesium and iron; electrolytes without limitation including sodium, potassium, magnesium, calcium, lithium, ammonium, phosphorous, chloride, iodide, bromide, fluoride, acetate, sulfate, carbonate, phosphate, lactate, gluconate and lactobionate; also carbohydrates; amino acids including leucine, isoleucine, lysine, methione, phenylalanine, threonine, tryptophan, valine, alanine, arginine, histidine, proline, serine, tyrosine, glycine, taurine and carnitine, as the L-, D- and racemic forms but particularly the L-acids and branched chain amino acids; also keto-analogs of all of the above listed amino acids; partial hydrolysates of proteins and oligo and poly-peptides of synthetic origin; also phospholipids without limitation. As an option, antioxidants, preferably a tocopherol, may be included in formulations of this invention which deliver nutrients.

To prepare freeze dry compositions of food, the following preferred process is used. (1) Freeze a unit of the food composition, e.g., whole milk, at 0° C. or below until the unit is converted into a frozen solid. (2) Next, dehydrate the frozen milk in an airtight container using anhydrous alcohol preferably in a weight ratio of alcohol to frozen milk of at least about 10:1 to achieve fast dehydration, as follows: Place the product of step (1) in a suitable plastic container which may be a fine mesh plastic bag or a plastic bottle containing multiple holes of ½ mm or less and immerse in a container of anhydrous ethyl alcohol maintained at a temperature of −15° C. or below The water content of the alcohol can be measured before this step. Step (2) continues until the water content of the alcohol is about 2.5% or more. The process of step (2) is repeated using a fresh supply of anhydrous alcohol. The process continues until about 100% of the water (ice) has been removed from the frozen milk. (3) Next, place the dehydrated frozen milk, e.g., in tablet form, resulting from step (2) on blotting paper and transfer quickly to a vacuum chamber. (4) Vacuum dry the product of step (3) at ambient temperature until no odor of the ethyl alcohol remains. Completion of step (4) produces a finished powdered product of freeze dried milk, a dry foodstuff. This product has the flavor of the natural product but has improved stability and an extended shelf life extending to 1 year or more.

To improve the stability and dispersibility of drug formulations, the following process is used. (1) Prepare a slurry of the desired drug using any liquid as the solvent, i.e., water, glycerin, and the like. Water is preferred. In the instance of water insoluble drugs, a suspension of the drug in water may be used. (2) Place the composition of step (1) in a suitable plastic container and follow the procedures described as steps (2), (3) and (4) described above with reference to the processing of frozen milk. The finished product comprises the desired drug in powdered form which may be placed in liquid or solid form and administered or stored. If packed under vacuum conditions the shelf life of the drug may extend to 3 years or more.

EXAMPLES

EXAMPLE 1

Mix the following ingredients together; 1 gram of flavored gelatin powder, 2 grams of maltodextrin, 0.5 gram of gelatin A; 2 grams of sucrose and 1 gram of aspartane. After mixing these components, add distilled water in an amount that will make a final volume of about 100 ml. Stir and heat the product to 60° C.; continue this step until it comprises a clear solution. Next cool the product to 37° C. Prepare blister molds to make the porous tablets by first rinsing the molds with a 10% solution of lecithin in 190 proof grain alcohol. Following the rinsing step, dry the mold at ambient temperature. Fill each compartment in the mold with 3 mls of the solution described immediately above. Next, store the product at a temperature of −10° C. or lower for 40 minutes. Remove the product from storage and add 300 mgs. of powdered acetominophen to the surface of each tablet within the mold. During this step the product must be protected from thawing. The product is then stored under refrigeration at −10° C. for 40 minutes.

Next, remove the product from storage and add 3 mls of the gelatin based solution described above to the upper surface of each frozen tablet in the mold. Refrigerate the product for 40 minutes at −10° C.

Transfer the frozen tablets from the mold to a mesh plastic bag. Immerse the bag and its contents in an air tight container of anhydrous ethyl alcohol maintained at a temperature of −20° C. The immersion step continues until tests reveal that the tablets are completely dehydrated. Replace the alcohol with fresh supplies of anydrous alcohol as required to facilitate dehydration. Continue this step until no odor or other evidence of alcohol can be detected. On completion of this step, the composition comprises a finished product.

EXAMPLE 2

Example 2 follows the procedure of Example 1 except that 250 mgs of powdered erythromycin is used in place of acetaminophen.

EXAMPLE 3

Example 3 follows the procedure of Example 1 except that aspartane is not used and the refrigeration temperatures −20° C. rather than −10° C.

EXAMPLE 4

Example 4 follows the procedure of Example 1 except that all the formulation steps are repeated prior to the immersing the product in anydrous ethyl alcohol. The finished product will comprise a six layer tablet.

EXAMPLE 5

The method of Example 1 is followed except that 300 mgs of acetaminphen is mixed into the gelatin based solution after it has cooled. The step of adding acetominophen to the surface of the frozen interin product is omitted.

EXAMPLE 6

The method of Example 1 is followed except that 300 mgs of acetaminophen is added to the cooled gelatin based solution. The finished product of this example contains 600 mgs of acetaminophen.

EXAMPLE 7

The method of Example 1 is followed except that two drops of cherry flavoring is added by pipette to the surface of each formed tablet.

EXAMPLE 8

The method of Example 1 is followed except that the finished tablets are processed by a granulator to produce a granular porous solid dosage form.

EXAMPLE 9

The method of Example 1 is followed except that a fine plastic mesh is used in place of the blister mold. The finished product comprises a powder form of the claimed composition.

EXAMPLE 10

The method of Example 1 is followed except that the following minerals are added to the cooled gelatin based solution: iodine 150 mcg; calcium, 1 mgm; magnesium 400 mg; manganese 3 mgs; iron 18 mg; copper 2 mg' zinc 15 mgs; and phosphorous, 1 gm. Store the product at 33° C. to give a slurry like consistency to the product. Following the first freezing step, a composition comprised of 500 mgs of Vitamin C, 15 units of Vitamin E; 15 mg Vitamin $B_1$; 17 mg Vitamin $B_2$; 100 mg niacin; 25 mg Vitamin $B_6$; 12 mcg Vitamin $B_{12}$, and 25 mg pantothenic acid is added to the surface of each semi-finished frozen tablet. The remaining processing steps of Example 1 are used as given. The step in Example 1 in which the drug is added is not used in this Example. In addition this Example illustrates a method wherein two groups of compositions which are incompatible from a manufacturing point of view can be prepared in a single tablet.

EXAMPLE 11

The method of Example 1 is followed except that the step in which acetaminophen is added is not used. In this example, 3.5 grams of Vivonex (Norwich-Eaton) is mixed into the cooling gelatin based solution and stored under refrigeration at 35° C to give a slurrylike consistency to the product. The blister molds are filled with 25 mls of this composition.

It will be understood that the present disclosure has been made only by way of a number of preferred embodiments and that numerous changes in details of construction, combination, and arrangement of parts can be resorted to without departing from the spirit and scope of the invention as hereunder claimed.

What is claimed and sought to be secured by Letters Patent of the United States is:

1. A method of manufacturing a carrier material having sufficient rigidity for carrying and administration of an active material selected from the group consisting of drugs, nutrients, vitamins, biologically-active compounds, foodstuffs, and combinations thereof comprising the steps of:
   (a) freezing a hydrated solution comprising a water-soluble gel or foam material and a monosaccharide or polysaccharide rigidifying agent for said gel or foam material;
   (b) contacting the frozen material of step (a) with the active material in an amount sufficient to cause the active material to be absorbed or absorbed within the frozen material;
   (c) dehydrating the frozen material from step (b) by causing material transfer of water from the frozen material to an organic liquid solvent while both the frozen material and the organic solvent are held at a temperature of about 0° C. or below; and
   (d) removing the organic liquid solvent from the dehydrated material resulting from step (c).

2. The method of claim 1 further including adding a flavoring material to the surface of the dehydrated material.

3. The method of claim 1 further including the step of adding a layer of the hydrated composition of step (a), in liquid form, onto the surface of the frozen composition resulting from step (a), and freezing the layers together.

4. The method of claim 3 including adding an active material to the frozen material resulting from step (a) prior to the addition of the layer of liquid composition.

5. The method of claim 4 further including adding an active material to the frozen material resulting from adding the layer of liquid over the frozen composition of step (a) either before or after freezing the added layer.

6. The method of claim 1 wherein the gel or foam material is a proteinacous material selected from the group consisting of gelatin, gelatin A, gelatin B, fluid gelatin, modified fluid gelatin, albumin, and lecithin.

7. The method of claim 2 wherein the rigidifying material is selected from the group consisting of a monosaccharide, a polysaccharide, and combinations thereof.

8. The method of claim 3 wherein the rigidifying material is selected from the group consisting of dextrose, fructose, galactose, mannitol, xylitol, sorbitol, sucrose, lactose, maltose, dextrans, dextran derivatives and combinations thereof.

9. The method of claim 4 wherein the rigidifying agent is maltodextrin.

10. The method of claim 5 wherein the maltodextrin has a weight average molecular weight of about 40,000 to about 90,000.

11. The method of claim 1 wherein the hydrated gel or foam material has been dehydrated in a frozen state by contact with an organic solvent having a freezing point below 0° C at near freezing temperature.

12. The method of claim 1 wherein the hydrated, frozen gel or foam material is dehydrated by immersing the frozen gel or foam material in a lower alcohol ($C_1$ to $C_5$) at a temperature of 0° C. or below.

* * * * *